United States Patent [19]
Hirota et al.

[11] Patent Number: 5,849,779
[45] Date of Patent: *Dec. 15, 1998

[54] PYRAZOLE DERIVATIVES AND THEIR PHARMACEUTICAL USE

[75] Inventors: Kohsaku Hirota; Hironao Sajiki, both of Gifu; Yoshiaki Isobe; Yoichi Ohba, both of Saitama; Hiroyuki Morita, Tokyo; Haruo Takaku; Nobuyoshi Chiba, both of Saitama, all of Japan

[73] Assignee: Japan Energy Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 864,076
[22] Filed: May 28, 1997

[30] Foreign Application Priority Data

May 29, 1996 [JP] Japan ................................. 8-135574
Oct. 23, 1996 [JP] Japan ................................. 8-281108

[51] Int. Cl.$^6$ ....................... C07D 231/04; A61K 31/415
[52] U.S. Cl. ....................... 514/407; 514/407; 548/371.7
[58] Field of Search ........................ 548/371.7; 514/407

[56] References Cited

FOREIGN PATENT DOCUMENTS

| 0667342A1 | 1/1995 | European Pat. Off. . |
| 1106330 | 5/1959 | Germany . |
| 56-156264 | 12/1981 | Japan ..................... C07D 231/40 |

OTHER PUBLICATIONS

Chemical Abstracts, 28–Heterocyclic Compounds (More Than One Hetero Atom) vol. 125, No. 25, 1996, p. 1390.
Chemical Abstracts, 28–Heterocyclic Compounds (More Than One Hetero Atom) vol. 125, No. 5, 1996, p. 1147.
Chemical Abstracts, vol. 86, 1977, p. 362.
Chemical Abstracts, vol. 76, 1972, p. 464.
Chemical Abstracts, 28–Heterocycles, vol. 106, 1987, p. 687.
Chemical Abstracts, vol. 101, 1984, p. 762.
Chemical Abstracts, vol. 98, 1983, p. 210.
Pharmazie, vol. 46, No. 10, Oct. 1991, pp. 747–748.
Senda et al, Chem. Pharm. Bull., 20(2) 391–398 (1972).

*Primary Examiner*—Johann Richter
*Assistant Examiner*—Joseph Murray
*Attorney, Agent, or Firm*—Fish & Richardson, P.C.

[57] ABSTRACT

The present invention relates to a pyrazole derivative represented by formula (I) or (II)

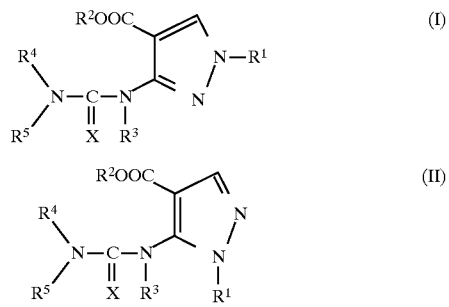

wherein $R^1$ is hydrogen C2–C6 alkyl benzyl or phenyl; each of $R^2$ and $R^3$ is hydrogen, C1–C6 alkyl or benzyl; each of $R^4$ and $R^5$ is hydrogen, C1–C6 alkyl, C3–C6 alkenyl, C3–C8 cycloalkyl, benzyl or phenyl;

X is oxygen or sulfur;

$R^5$ is hydrogen, C2–C6 alkyl, C3–C6 alkenyl, C3–C8 cycloalkyl or benzyl when $R^1$ is benzyl, $R^2$ is ethyl, $R^3$ is hydrogen, and $R^4$ is hydrogen, and its pharmaceutical use.

8 Claims, No Drawings

PYRAZOLE DERIVATIVES AND THEIR PHARMACEUTICAL USE

BACKGROUND OF THE INVENTION

1. Field of the Invention

The present invention relates to a novel pyrazole derivative and its pharmaceutical use, concretely, an inhibitor of smooth muscle cell growth comprising said pyrazole derivative as the active ingredient and a pharmaceutical composition comprising said pyrazole derivative as the active ingredient for prevention or cure of diseases caused by smooth muscle cell growth, particularly, vascular re-narrowing after percutaneous transluminal coronary angioplasty, vascular re-narrowing after percutaneous transluminal angioplasty, membrane proliferative nephritis, arterioscleotic diseases, hypertension, or diabetes mellitus.

2. Description of the Prior Art

Ischemic heart diseases such as myocardial infarction and angina pectoris are obstructive disease of coronary artery which are caused by narrowing of coronary artery induced by cholesterol deposition etc. To these obstructive disease of coronary artery, treatment by thrombus resolvents such as t-PA or operation by percutaneous transluminal coronary angioplasty (PTCA) or percutaneous transluminal angioplasty are applied. Particularly, operative angioplasty has spread in recent years because of its immediate clinical effect. In said angioplasty, narrow vascular segment is physically dilated by an inflating balloon which is inserted with a catheter through femoral artery etc. However, a serious problem of said angioplasty is that re-narrowing often occur 3–6 month after the operation [Circulation, 84, 1426–1436 (1991); Drugs, 46, 259–262 (1993)].

Immediate thrombotic re-occlusion after the angioplasty is caused by excessive adhesion/aggregation of platelets on the vascular inside injured by the angioplasty. In contrast with the acute occlusion, the above mentioned delayed re-narrowing is said to be caused by endarterial hypertrophy induced by abnormal growth/ wandering of smooth muscle cell and smooth muscle cell-produced intercellular matrix on the occasion of endarterial injury. The endarterial hypertrophy also causes membrane proliferative nephritis, arterioscleotic diseases, diabetes mellitus, hypertension, and so on. Growth factors of smooth muscle cell such as platelet-derived growth factor (PDGF), Epidermal Growth Factor (EGF), and insulin-like growth factor (IGF) are known. Although antagonistic agents against said growth factors can inhibit growth of smooth muscle cell, no drug has been clinically practicable. Trapidil, which has PDGF inhibitory activity [Life Sciences, 28, 1641–1646 (1981)], is effective against animal model of re-narrowing [Circulation, 81, 1089–1093 (1990)]. However, it has not been practicable because of its insufficient activity. Tranilast, which has been clinically used as anti-allergy drug, was recently reported to inhibit growth of smooth muscle cell [Atherosclerosis, 107, 179–185 (1994)] and to prevent clinical re-narrowing after percutaneous transluminal angioplasty [Rinsho Iyaku, 12, 65–85 (1996)]. It has been known that tranilast often causes side effects on hepatic function, and most careful use is required despite of its distinct effect.

On the above mentioned condition, development of a new drug which shows superior inhibition of smooth muscle cell growth induced by growth factors, such as PDGF, is desired. In addition, because vascular re-narrowing after percutaneous transluminal coronary angioplasty or percutaneous transluminal angioplasty attends chronic disease such as myocardial infarction and angina pectoris, the inhibitor of smooth muscle cell growth is required to have safety upon extended or repeated administration. The similar safety is required for the use against diseases such as membrane proliferative nephritis, arterioscleotic diseases, diabetes mellitus, and hypertension.

OBJECTS AND SUMMARY OF THE INVENTION

The present invention purpose to offer a compound which inhibits growth of smooth muscle cell and a pharmaceutical composition comprising said compound as the active ingredient for prevention or cure of diseases caused by smooth muscle cell growth.

The inventors found that a pyrazole derivative having a specific structure inhibits smooth muscle cell growth and completed the invention.

The compound of the present invention is a pyrazole derivative represented by the following general formula (I) or the following general formula (II):

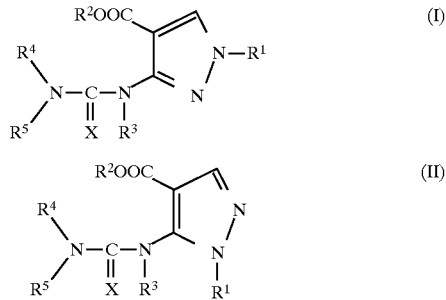

wherein $R^1$ is a hydrogen atom, a linear or branched C2–C6 alkyl group, a benzyl group, or a phenyl group; each of $R^2$ and $R^3$ is a hydrogen atom, a linear or branched C1–C6 alkyl group, or a benzyl group; each of $R^4$ and $R^5$ is a hydrogen atom, a linear or branched C1–C6 alkyl group, a linear or branched C3–C6 alkenyl group, a C3–C8 cycloalkyl group, a benzyl group, or a phenyl group;

X is an oxygen atom or a sulfur atom;

$R^5$ is a hydrogen atom, a linear or branched C2–C6 alkyl group, a linear or branched C3–C6 alkenyl group, a C3–C8 cycloalkyl group, or a benzyl group when $R^1$ is a benzyl group, $R^2$ is an ethyl group, $R^3$ is a hydrogen atom, and $R^4$ is a hydrogen atom, or a pharmaceutically acceptable salt thereof.

The present invention is pharmaceutically used as an inhibitor of smooth muscle cell growth and a pharmaceutical composition for prevention or cure of diseases caused by smooth muscle cell growth which comprises the above mentioned pyrazole derivative or a pharmaceutically acceptable salt thereof as the active ingredient. Typical diseases caused by smooth muscle cell growth are vascular re-narrowing after percutaneous transluminal coronary angioplasty, vascular re-narrowing after percutaneous transluminal angioplasty, membrane proliferative nephritis, arterioscleotic diseases, hypertension, diabetes mellitus, and so on. That is, the pharmaceutical composition of the present invention is used for prevention or cure of said diseases.

In the pyrazole derivative of the present invention, that is, the pyrazole derivative represented by above formula (I) or (II), a linear or branched C1–C6 alkyl group is a linear alkyl group such as methyl group, ethyl group, propyl group, butyl group, pentyl group, and hexyl group; or a branched alkyl group such as isopropyl group, isobutyl group, sec-butyl group, tert-butyl group, 1-methylbutyl group, 2-methylbutyl group, 3-methylbutyl group, 1,1dimethylpropyl group, 2,2-dimethylpropyl group, 1,2dimethylpropyl group, 1ethylpropyl group, 1-methylpentyl group, 2-methylpentyl group, 3-methylpentyl group, 4methylpentyl group, 1,1dimethylbutyl group, 1,2dimethylbutyl group, 1,3dimethylbutyl group, 1-ethylbutyl group, 2-ethylbutyl group, and 1ethyl-2-methylpropyl group. A linear or branched C2–C6 alkyl group is said linear or branched C1–C6 alkyl group except methyl group. A linear or branched C3–C6 alkenyl group has a carbon skeleton corresponding to said linear or branched C3–C6 alkyl group and a C—C double bond. They are, for example, an allyl group (2-propenyl group), a 1-propenyl group, an isopropenyl group, a 2-butenyl group, and a 2-pentenyl group. Among them, alkenyl group without double bond at C-1, such as an allyl group (2-propenyl group), a 2-butenyl group, and a 2-pentenyl group, can be used similarly to the corresponding alkyl group. That is, substituent effect of said alkenyl group without double bond at C-1 is similar to the corresponding saturated alkyl group. A C3–C8 cycloalkyl group is a monocyclic cycloalkyl group, that is, a cyclopropyl group, a cyclobutyl group, a cyclopentyl group, a cyclohexyl group, a cycloheptyl group, or a cyclooctyl group. Said monocyclic cycloalkyl group may have a linear or branched alkyl group as a side chain, and its total carbon number is not more than 8.

Out of the pyrazole derivative of the present invention, as the pyrazole derivative represented by formula (I), the compound wherein $R^1$ is a linear or branched C2–C6 alkyl group, or a benzyl group is more preferred. As the pyrazole derivative represented by formula (II), the compound wherein $R^1$ is a linear or branched C2–C6 alkyl group, a benzyl group, or a phenyl group is more preferred. Further, as the pyrazole derivative represented by formula (I) or (II), the compound wherein at least one of $R^4$ and $R^5$ is not a hydrogen atom is more preferred.

Some compounds having structural resemblance to a pyrazole derivative of formula (I) or formula (II) of the present invention have been reported [e.g. Chem. Pharm. Bull., 20, 391–397 (1972)]. Those reports, however, were made from synthetic interest, and nothing has been reported about biological activity of said known compound especially about inhibition of smooth muscle cell growth. Outline of methods to prepare the pyrazole derivative of the present invention is mentioned below.

First, a 3-ethoxy-2-cyanopropenoate represented by the following formula (III), e.g. ethyl 3-ethoxy-2-cyanopropenoate, and an unsubstituted or monosubstituted hydrazine represented by the following formula (IV) are cyclized to give a 3-amino-4-alkoxycarbonylpyrazole-type intermediate represented by the following formula (V), e.g. 3-amino-4-ethoxycarbonylpyrazole, or a 1-substituted 5-amino-4-alkoxycarbonylpyrazole-type intermediate represented by the following formula (VIb). In said formulae (III), (IV), (V), and (VIb), $R^1$ and $R^2$ each represents a group defined for the formulae (I) and (II).

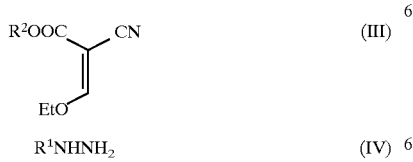

R¹NHNH₂    (IV)

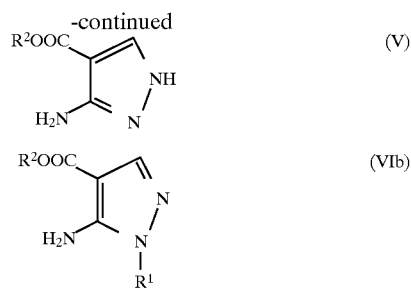

Lower alcohol, such as methanol and ethanol, is used as a solvent for this cyclization reaction, and reaction temperature is selected between room temperature and reflux temperature.

Second; the intermediate of formula (V) is reacted with an alkylating agent in the presence of a base to afford a 1substituted 3-amino-4-alkoxycarbonylpyrazole-type compound represented by the following formula (VIa) wherein $R^1$ and $R^2$ each represents a group defined for formula (I).

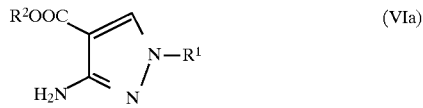

The newly introduced substituent $R^1$ is a hydrocarbon group derived from the alkylating agent, and a common alkylating agent such as alkyl halide, alkyl sulfate, and benzyl halide or the like can be used as the reagent for introduction of the substituent $R^1$. On the other hand, sodium hydroxide, alkoxides such as sodium methoxide and sodium ethoxide, or sodium hydride can be exemplified as the base, and said base can be selected suitably for the reagent used.

A solvent for the N-substitution is selected to be suitable for the base and the reagent such as the alkylating agent from water, alcohol, dimethylformamide, and so on. Reaction temperature is selected between room temperature and reflux temperature. A certain selection of the reagent, e.g. said alkylating agent, and the reaction temperature affords the compound of the formula (VIb) as a by-product along with the main product of the formula (VIa). They are separable by re-crystallization or column chromatography.

The intermediate of the formula (V), (VIa) or (VIb) can be further reacted with an alkylating agent or a benzylating agent in the presence of a base to afford introduction of the substituent $R^3$ into an amino group of said intermediate. The newly introduced substituent $R^3$ is a hydrocarbon group derived from the alkylating agent or the benzylating agent, and an alkylating agent such as alkyl halide, alkyl sulfate, and a benzylating agent such as benzyl halide can be used as the reagent for introduction of the substituent $R^3$. Sodium hydroxide, alkoxides such as sodium methoxide and sodium ethoxide, or sodium hydride can be exemplified as the base. A solvent for the reaction is selected to be suitable for the base and the reagent such as the alkylating agent from alcohol, dimethylformamide, and so on. Reaction temperature is selected between room temperature and reflux temperature.

The 1-substituted 3-amino-4-alkoxycarbonylpyrazole-type compound of the formula (VIa) can be reacted with an isocyanate or an isothiocyanate represented by the following formula (VII), wherein $R^4$ and X are as defined for the formula (I), in the presence of a base to afford a urea or a thiourea of the formula (I) in which $R^5$ is a hydrogen atom.

A trialkylamine such as triethylamine and dipropylethylamine which is a tertiary amine, is preferable as said base. An aprotic solvent, which can dissolve the above mentioned tertiary amine base, such as aromatic hydrocarbon, e.g. benzene and toluene, and cyclic ether, e.g. tetrahydrofuran and 1,4-dioxane, can be exemplified as a solvent. Reaction temperature is selected between room temperature and reflux temperature, and reaction under higher pressure, e.g. in a sealed tube, is more preferable.

The 1-substituted 3-amino-4-alkoxycarbonylpyrazole-type compound of the formula (VIa) can be reacted with triphosgene, $CO(OCCl_3)_2$, in the presence of a base to afford a compound represented by the following formula (VIIIa) or (VIIIb) wherein $R^1$ and $R^2$ are as defined for the formula (I).

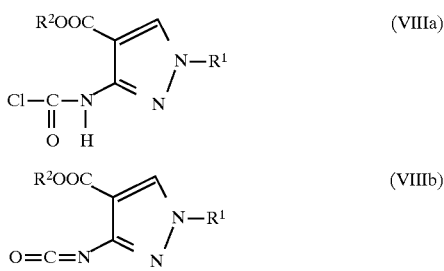

The compound of the formula (VIII) can be reacted with a primary amine represented by the following formula (IX), wherein $R^4$ is as defined for the formula (I), to afford the compound of the formula (I) wherein $R^5$ is a hydrogen atom and X is an oxygen atom.

The compound of the formula (VIII) can also be reacted with a secondary amine represented by the following formula (X), wherein $R^4$ and $R^5$ are as defined for the formula (I), to afford the compound of the formula (I) wherein X is an oxygen atom.

When a hydrogen atom is selected for $R^2$ of the compound of the formula (I), a carboxyl group can be protected by benzyl group during the above mentioned process. Said benzyl ester can be deprotected by catalytic hydrogenolysis using a catalyst such as Pd/C.

The compound of the formula (II) can be synthesized by the similar method using a 1substituted 5amino-4-alkoxycarbonylpyrazole-type compound of the formula (VIb) instead of a 1substituted 3-amino-4-alkoxycarbonylpyrazole-type compound of the formula (VIa).

In the pyrazole derivative of the formula (I) or (II) produced by the above mentioned method, the substituents $R^1$, $R^2$, $R^3$, $R^4$, and $R^5$ which characterize the structure of said pyrazole derivative are derived from the corresponding starting material, and their positions are specified. Structure of said pyrazole derivative can be easily confirmed by e.g. $^1H$-NMR.

Examples of the pyrazole derivative of the formula (I) or (II) are given below.

As the pyrazole derivative of the formula (I) having a urea-structure,
N-phenyl-N'-(4-ethoxycarbonyl-1-phenylpyrazol-3-yl)urea,
N-phenyl-N'-(1-butyl-4-ethoxycarbonylpyrazol-3-yl)urea,
N-isopropyl-N'-(1-benzyl-4-ethoxycarbonylpyrazol-3yl) urea,
N-tert-butyl-N'-(1-benzyl-4-ethoxycarbonylpyrazol-3-yl) urea,
N-2-propenyl-N'-(1-benzyl-4-ethoxycarbonylpyrazol-3-yl) urea,
N-benzyl-N'-(1-benzyl-4-ethoxycarbonylpyrazol-3-yl)urea,
N-propyl-N'-(1-benzyl-4-ethoxycarbonylpyrazol-3-yl)urea,
N-butyl-N'-(1-benzyl-4-ethoxycarbonylpyrazol-3-yl)urea,
N-hexyl-N'-(1-benzyl-4-ethoxycarbonylpyrazol-3-yl)urea,
N-cyclohexyl-N'-(1-benzyl-4-ethoxycarbonylpyrazol-3-yl) urea,
N-propyl-N'-(1-ethyl-4-ethoxycarbonylpyrazol-3-yl)urea,
N-butyl-N'-(1-ethyl-4-ethoxycarbonylpyrazol-3-yl)urea,
N-hexyl-N'-(1-ethyl-4-ethoxycarbonylpyrazol-3-yl)urea,
N-cyclohexyl-N'-(1-ethyl-4-ethoxycarbonylpyrazol-3-yl) urea,
N-propyl-N'-(4-ethoxycarbonyl-1-propylpyrazol-3-yl)urea,
N-butyl-N'-(4-ethoxycarbonyl-1-propylpyrazol-3-yl)urea,
N-hexyl-N'-(4-ethoxycarbonyl-1-propylpyrazol-3-yl)urea,
N-cyclohexyl-N'-(4-ethoxycarbonyl-1-propylpyrazol-3-yl) urea,
N-propyl-N'-(1-butyl-4-ethoxycarbonylpyrazol-3-yl)urea,
N-butyl-N'-(1-butyl-4-ethoxycarbonylpyrazol-3-yl)urea,
N-hexyl-N'-(1-butyl-4-ethoxycarbonylpyrazol-3-yl)urea,
N-cyclohexyl-N'-(1butyl-4-ethoxycarbonylpyrazol-3-yl) urea,
N-propyl-N'-(1-benzyl-4carboxypyrazol-3-yl)urea,
N-butyl-N'-(1-benzyl-4-carboxypyrazol-3-yl)urea,
N-hexyl-N'-(1-benzyl-4-carboxypyrazol-3-yl)urea,
N-cyclohexyl-N'-(1-benzyl-4-carboxypyrazol-3-yl)urea,
N-propyl-N'-(4-carboxy-1-ethylpyrazol-3-yl)urea,
N-butyl-N'-(4-carboxy-1ethylpyrazol-3-yl)urea,
N-hexyl-N'-(4-carboxy-1ethylpyrazol-3-yl)urea,
N-cyclohexyl-N'-(4-carboxy-1ethylpyrazol-3-yl)urea,
N-propyl-N'-(4-carboxy-1-propylpyrazol-3-yl)urea,
N-butyl-N'-(4-carboxy-1-propylpyrazol-3-yl)urea,
N-hexyl-N'-(4-carboxy-1-propylpyrazol-3-yl)urea,
N-cyclohexyl-N'-(4-carboxy-1-propylpyrazol-3-yl)urea,
N-propyl-N'-(1-butyl-4carboxypyrazol-3-yl)urea,
N-butyl-N'-(1-butyl-4carboxypyrazol-3-yl)urea,
N-hexyl-N'-(1-butyl-4carboxypyrazol-3-yl)urea,
N-cyclohexyl-N'-(1-butyl-4carboxypyrazol-3-yl)urea,
N, N-dimethyl-N'-(1-benzyl-4-ethoxycarbonylpyrazol-3-yl) urea,
N, N-dipropyl-N'-(1-benzyl-4-ethoxycarbonylpyrazol-3-yl) urea,
N, N-dibutyl-N'-(1-benzyl-4-ethoxycarbonylpyrazol-3-yl) urea,
N, N-diphenyl-N'-(1-benzyl-4-ethoxycarbonylpyrazol-3-yl) urea,
N, N-dicyclohexyl-N'-(1-benzyl-4-ethoxycarbonylpyrazol-3-yl)urea,
N, N-dimethyl-N'-(4-ethoxycarbonyl-1-propylpyrazol-3-yl) urea,
N, N-dipropyl-N'-(4-ethoxycarbonyl-1-propylpyrazol-3-yl) urea,
N, N-dibutyl-N'-(4-ethoxycarbonyl-1-propylpyrazol-3-yl) urea,
N, N-diphenyl-N'-(4-ethoxycarbonyl-1-propylpyrazol-3-yl) urea,
N, N-dicyclohexyl-N'-(4-ethoxycarbonyl-1-propylpyrazol-3-yl)urea,
N, N-dimethyl-N'-(1-butyl-4-ethoxycarbonylpyrazol-3-yl) urea,
N, N-dipropyl-N'-(1-butyl-4-ethoxycarbonylpyrazol-3-yl) urea,
N, N-dibutyl-N'-(1-butyl-4-ethoxycarbonylpyrazol-3-yl) urea,
N, N-diphenyl-N'-(1-butyl-4-ethoxycarbonylpyrazol-3-yl) urea, N,N-dicyclohexyl-N'-(1-butyl-4-ethoxycarbonylpyrazol-3-yl)urea,
N-propyl-N'-(1-benzyl-4-ethoxycarbonylpyrazol-3-yl)-N'-methylurea,
and N-propyl-N'-benzyl-N'-(1-benzyl-4-ethoxycarbonylpyrazol-3-yl)urea can be exemplified.

As the pyrazole derivative of the formula (I) having a thiourea-structure,
N-phenyl-N'-(1-butyl-4-ethoxycarbonylpyrazol-3-yl)thiourea,
N-propyl-N'-(1-benzyl-4-ethoxycarbonylpyrazol-3-yl)thiourea,
N-butyl-N'-(1-benzyl-4-ethoxycarbonylpyrazol-3-yl)thiourea,
N-hexyl-N'-(1-benzyl-4-ethoxycarbonylpyrazol-3-yl)thiourea,
N-cyclohexyl-N'-(1-benzyl-4-ethoxycarbonylpyrazol-3-yl)thiourea,
N-propyl-N'-(1-ethyl-4-ethoxycarbonylpyrazol-3-yl)thiourea,
N-butyl-N'-(1-ethyl-4-ethoxycarbonylpyrazol-3-yl)thiourea,
N-hexyl-N'-(1-ethyl-4-ethoxycarbonylpyrazol-3-yl)thiourea,
N-cyclohexyl-N'-(1-ethyl-4-ethoxycarbonylpyrazol-3-yl)thiourea,
N-propyl-N'-(4-ethoxycarbonyl-1-propylpyrazol-3-yl)thiourea,
N-butyl-N'-(4-ethoxycarbonyl-1-propylpyrazol-3-yl)thiourea,
N-hexyl-N'-(4-ethoxycarbonyl-1-propylpyrazol-3-yl)thiourea,
N-cyclohexyl-N'-(4-ethoxycarbonyl-1-propylpyrazol-3-yl)thiourea,
N-propyl-N'-(1-butyl-4-ethoxycarbonylpyrazol-3-yl)thiourea,
N-butyl-N'-(1-butyl-4-ethoxycarbonylpyrazol-3-yl)thiourea,
N-hexyl-N'-(1-butyl-4-ethoxycarbonylpyrazol-3-yl)thiourea,
N-cyclohexyl-N'-(1-butyl-4-ethoxycarbonylpyrazol-3-yl)thiourea,
N-propyl-N'-(1-benzyl-4carboxypyrazol-3-yl)thiourea,
N-butyl-N'-(1-benzyl-4carboxypyrazol-3-yl)thiourea,
N-hexyl-N'-(1-benzyl-4carboxypyrazol-3-yl)thiourea,
N-cyclohexyl-N'-(1-benzyl-4carboxypyrazol-3-yl)thiourea,
N-propyl-N'-(4-carboxy-1ethylpyrazol-3-yl)thiourea,
N-butyl-N'-(4-carboxy-1-ethylpyrazol-3-yl)thiourea,
N-hexyl-N'-(4-carboxy-1-ethylpyrazol-3-yl)thiourea,
N-cyclohexyl-N'-(4-carboxy-1-ethylpyrazol-3-yl)thiourea,
N-propyl-N'-(4-carboxy-1-propylpyrazol-3-yl)thiourea,
N-butyl-N'-(4-carboxy-1-propylpyrazol-3-yl)thiourea,
N-hexyl-N'-(4-carboxy-1-propylpyrazol-3-yl)thiourea,
N-cyclohexyl-N'-(4-carboxy-1-propylpyrazol-3-yl)thiourea,
N-propyl-N'-(1-butyl-4-carboxypyrazol-3-yl)thiourea,
N-butyl-N'-(1-butyl-4-carboxypyrazol-3-yl)thiourea,
N-hexyl-N'-(1-butyl-4-carboxypyrazol-3-yl)thiourea,
N-cyclohexyl-N'-(1-butyl-4-carboxypyrazol-3-yl)thiourea,
N-dimethyl-N'-(1-benzyl-4-ethoxycarbonylpyrazol-3-yl)thiourea,
N-dimethyl-N'-(1-benzyl-4-ethoxycarbonylpyrazol-3-yl)thiourea,
N,N-dipropyl-N'-(1-benzyl-4-ethoxycarbonylpyrazol-3-yl)thiourea,
N,N-dibutyl-N'-(1-benzyl-4-ethoxycarbonylpyrazol-3-yl)thiourea,
N,N-diphenyl-N'-(1-benzyl-4-ethoxycarbonylpyrazol-3-yl)thiourea,
N,N-dicyclohexyl-N'-(1-benzyl-4-ethoxycarbonylpyrazol-3-yl)thiourea,
N,N-dimethyl-N'-(4-ethoxycarbonyl-1-propylpyrazol-3-yl)thiourea,
N,N-dipropyl-N'-(4-ethoxycarbonyl-1-propylpyrazol-3-yl)thiourea,
N,N-dibutyl-N'-(4-ethoxycarbonyl-1-propylpyrazol-3-yl)thiourea,
N,N-diphenyl-N'-(4-ethoxycarbonyl-1-propylpyrazol-3-yl)thiourea,
N,N-dicyclohexyl-N'-(4-ethoxycarbonyl-1-propylpyrazol-3-yl)thiourea,
N,N-dipropyl-N'-(1-butyl-4-ethoxycarbonylpyrazol-3-yl)thiourea,
N,N-dibutyl-N'-(1-butyl-4-ethoxycarbonylpyrazol-3-yl)thiourea,
N,N-diphenyl-N'-(1-butyl-4-ethoxycarbonylpyrazol-3-yl)thiourea,
N,N-dicyclohexyl-N'-(1-butyl-4-ethoxycarbonylpyrazol-3-yl)thiourea,
N-propyl-N'-(1-benzyl-4-ethoxycarbonylpyrazol-3-yl)-N'-methylthiourea,
and N-propyl-N'-benzyl-N'-(1-benzyl-4-ethoxycarbonylpyrazol-3-yl)thiourea can be exemplified.

As the pyrazole derivative of the formula (II) having a urea-structure,
N-propyl-N'-(1-benzyl-4-ethoxycarbonylpyrazol-5-yl)-N'-methylurea,
N-propyl-N'-benzyl-N'-(1-benzyl-4-ethoxycarbonylpyrazol5-yl)urea,
N-phenyl-N'-(1-benzyl-4-ethoxycarbonylpyrazol-5-yl)urea,
N-propyl-N'-(1-benzyl-4-ethoxycarbonylpyrazol-5-yl)urea,
N-phenyl-N'-(4-ethoxycarbonyl-1-phenylpyrazol-5-yl)urea,
and N-propyl-N'-(4-ethoxycarbonyl-1-phenylpyrazol-5-yl)urea
can be exemplified.

As the pyrazole derivative of the formula (II) having a thiourea-structure,
N-propyl-N'-(1benzyl-4-ethoxycarbonylpyrazol-5-yl)-N'-methylthiourea,
N-propyl-N'-benzyl-N'-(1benzyl-4-ethoxycarbonylpyrazol-5-yl)thiourea,
N-phenyl-N'-(1-benzyl-4-ethoxycarbonylpyrazol-5-yl)thiourea,
N-propyl-N'-(1-benzyl-4-ethoxycarbonylpyrazol-5-yl)thiourea,
N-phenyl-N'-(4-ethoxycarbonyl-1-phenylpyrazol-5-yl)thiourea,
and N-propyl-N'-(4-ethoxycarbonyl-1-phenylpyrazol-5-yl)thiourea can be exemplified.

As the pharmaceutically acceptable salt of the above mentioned pyrazole derivative, a hydrochloride, a sulfate, a nitrate, a methanesulfonate, a toluenesulfonate, a sodium salt, a potassium salt, and a calcium salt can be exemplified.

The pharmaceutical composition of the present invention for prevention or cure of diseases caused by smooth muscle cell growth comprises the above mentioned pyrazole derivative which inhibit smooth muscle cell growth as the active ingredient. Said active ingredient is mixed with additives such as a excipient to make the composition. Symptoms of diseases against which said pharmaceutical composition are applied, those are, vascular re-narrowing after percutaneous transluminal coronary angioplasty, vascular re-narrowing after percutaneous transluminal angioplasty, membrane proliferative nephritis, arterioscleotic diseases, and so on, appear gradually. The pharmaceutical composition of the present invention is mainly administered to arrest said symptoms. From the viewpoint of said usage, oral formulation is most preferable. Therefore, dosage forms, carriers, and additives which are usually used in oral formulations, are preferably used. For example, powders, tablets, or capsules can be made with excipients such as lactose. Dose of the pyrazole derivative, the active ingredient, should be suitably selected for age, sex, and body weight of patients; purpose of administration; or seriousness of diseases. In general, dose is selected between 0.1 and 100 mg/kg of the pyrazole derivative per day in a male adult, and said dose is administered once a day or divided into several times a day.

The pyrazole derivative of the present invention has potent inhibitory activity against smooth muscle cell growth induced by cell growth factors such as PDGF. Therefore, it is useful for prevention and cure of diseases caused by smooth muscle cell growth, such as, vascular re-narrowing after percutaneous transluminal coronary angioplasty, vascular re-narrowing after percutaneous transluminal angioplasty, membrane proliferative nephritis, arteriosclerotic diseases, diabetes mellitus, and hypertension.

DESCRIPTION OF THE PREFERRED EMBODIMENTS

The present invention is further explained in detail by the following examples. The invention is not restricted to the examples.

(EXAMPLE 1)

N-propyl-N'-(1-benzyl-4-ethoxycarbonylpyrazol-3-yl)urea

To a solution of ethyl (ethoxymethylene)cyanoacetate (10 g) in ethanol (100 ml), was added hydrazine monohydrate (2.87 ml), and the resulted mixture was refluxed for 12 h. The reaction mixture was evaporated under reduced pressure followed by addition of ether (50 ml), and 3-amino-4-ethoxycarbonylpyrazole was obtained as pale yellow crystals (7.68 g, yield 84%).

Sodium (1.9 g) was dissolved in anhydrous ethanol (100 ml) to prepare a solution of sodium ethoxide. To this, were added 3-amino-4-ethoxycarbonylpyrazole (12.4 g) and benzyl chloride (10 g), and the resulted mixture was refluxed for 1 h. After filtration of the hot mixture, the filtrate was concentrated to quarter volume, and cooled to crystallize. The crude product was recrystallized from an ether-water mixture to give 3-amino-1-benzyl-4-ethoxycarbonylpyrazole (10.7 g, yield 44%). To a solution of 3-amino-1-benzyl-4-ethoxycarbonylpyrazole (0.2 g) in dried toluene (30 ml), were added propyl isocyanate (0.307 ml) and triethylamine (0.11 ml), and the mixture was refluxed in a sealed tube for 8 h. The reaction mixture was evaporated under reduced pressure followed by silica-gel column chromatography (toluene : ethyl acetate=20:1) to give the title compound (0.129 g, yield 48%). $^1$H-NMR (CDCl$_3$) δ ppm: 0.92 (3H, t, J=7Hz, CH$_2$CH$_2$CH$_3$), 1.32 (3H, t, J=7Hz, COOCH$_2$CH$_3$), 1.57 (2H, 6th, CH$_2$CH$_2$CH$_3$), 4.28 (2H, q, J=7Hz, COOCH$_2$CH$_3$), 5.14 (2H, s, CH$_2$—Ph), 7.25 (5H, m, CH$_2$—Ph), 7.91 (2H, brs, NH), 8.00 (1H, s, C5-H)

Mass (m/z): 330 (M$^+$)

Anal.: C$_{17}$ H$_{22}$ N$_4$ O$_3$ calcd. C, 61.80; H, 6.71; N, 16.96 found. C, 61.66; H, 6.85; N, 16.99 m.p.: 100°–101° C.

(EXAMPLE 2)

N-phenyl-N'-(1-butyl-4-ethoxycarbonylpyrazol-3-yl)urea

The title compound was prepared by the similar method to Example 1 (yield 18%).

$^1$H-NMR (CDCl$_3$) δ ppm: 1.00 (3H, t, J=8Hz, CH$_2$CH$_2$CH$_2$CH$_3$), 1.25 (6H, t and 6th, CH$_2$CH$_2$CH$_2$CH$_3$ and COOCH$_2$CH$_3$), 1.84 (2H, 5th, CH$_2$CH$_2$CH$_2$CH$_3$), 4.05 (2H, t, J=7Hz, CH$_2$CH$_2$CH$_2$CH$_2$CH$_3$), 4.30 (2H, q, J=7Hz, COOCH$_2$CH$_3$), 7.20 (5H,m, Ph), 7.75 (1H ,s, C5-H), 8.20 (1H,brs, NH), 10.15 (1H,brs, NH)

Mass (m/z): 330 (M$^+$)

Anal.: C$_{17}$ H$_{22}$ N$_4$ O$_3$ calcd. C, 61.80; H, 6.71; N, 16.96 found. C, 61.89; H, 6.71; N, 16.95 m.p.: 118°–120° C.

(EXAMPLE 3)

N-phenyl-N'-(1-butyl-4-ethoxycarbonylpyrazol-3-yl)thiourea

The title compound was prepared by the similar method to Example 1 (yield 58%).

$^1$H-NMR (CDCl$_3$) δ ppm: 0.95 (3H, t, J=7Hz, CH$_2$CH$_2$CH$_2$CH$_3$), 1.40 (6H, t and 6th, J=7Hz, CH$_2$CH$_2$CH$_2$CH$_3$ and COOCH$_2$ CH$_3$), 1.85 (2H, 5th, CH$_2$CH$_2$CH$_2$CH$_3$), 4.05 (2H, t, J=7Hz, CH$_2$CH$_2$CH$_2$CH$_3$), 4.35 (2H, q, J=7Hz, COOCH$_2$CH$_3$), 7.30 (5H, m, Ph), 7.77 (1H, s, C5-H), 9.53 (1H, brs, NH)

Mass (m/z): 346 (M$^+$)

Anal.: C$_{17}$H$_{22}$N$_4$ O$_2$ S calcd. C, 58.93; H, 6.41; N, 16.18 found. C, 58.74; H, 6.36; N, 16.20 m.p.: 93°–95° C.

(REFERENCE EXAMPLE 1)

N-phenyl-N'-(1-benzyl-4-ethoxycarbonylpyrazol-3-yl)urea

To a solution of triphosgene (35.7 mg) in THF (2 ml), was slowly added a solution of 3-amino-1-benzyl-4-ethoxycarbonylpyrazole (30 mg) and diisopropylethylamine (0.0936 ml) in THF (1 ml) over 15 min, and the resulted mixture was stirred at 40° C. for 5 h. To this, was added a solution of aniline (0.0111 ml) and diisopropylethylamine (0.0936 ml) in THF (1 ml), and the resulted mixture was further stirred to react. After completion of the reaction, water was added followed by evaporation under reduced pressure. Ether was added to the residue to crystallize the title compound (32 mg, yield 71%). The product gave the similar $^1$H-NMR spectrum to an authentic sample prepared by a reported method [Chem. Pharm. Bull., 20, 391–397 (1972)].

(EXAMPLE 4)

N-phenyl-N'-(1-benzyl-4-benzyloxycarbonylpyrazol-3-yl)urea

The title compound was prepared by the similar method to Reference Example 1 (yield 80%) from 3-amino-4-benzyloxycarbonylpyrazole obtained by the similar method to Example 1.

$^1$H-NMR (CDCl$_3$) δ ppm: 5.22 (2H, s, COOCH$_2$Ph), 5.47 (2H, s, N—CH$_2$Ph), 7.50 (15H, m, N—CH$_2$Ph and 3-NHCONHPh and COOCH$_2$Ph), 7.88 (1H, s, C5-H)

Mass (m/z): 426 (M$^+$)

Anal.: C$_{25}$ H$_{22}$ N$_4$ O$_3$ calcd. C, 70.41; H, 5.20; N, 13.14 found. C, 70.20; H, 5.18; N, 13.16

(EXAMPLE 5)

N-phenyl-N'-(1-benzyl-4-carboxypyrazol-3-yl)urea

A mixture of the compound of Example 4 (300 mg, 0.7 mmol), DMF (5 ml), methanol (40 ml), and 5% Pd/C (30 mg) was stirred for 24 h under hydrogen. After filtration of the reaction mixture, the filtrate was evaporated under reduced pressure to give the title compound (203 mg, yield 86%).

$^1$H-NMR (DMSO-d6) δ ppm: 5.37 (2H, s, N—CH$_2$Ph), 7.90 (10H, m, N—CH$_2$Ph and 3-NHCONHPh), 7.89 (1H, s, C5-H), 8.59 (1H, brs, NH), 9.92 (1H, brs, NH)

Mass (m/z): 336 (M$^+$)

Anal.: C$_{18}$ H$_{16}$ N$_4$ O$_3$ calcd. C, 64.28; H, 4.79; N, 16.66 found. C, 64.17; H, 4.94; N, 16.61

(REFERENCE EXAMPLE 2)

N-phenyl-N'-(4-ethoxycarbonyl-1-methylpyrazol-5-yl)urea

To a solution of ethyl 3-ethoxy-2-cyanopropenoate (5.14 g) in ethanol (50 ml), was added methylhydrazine (1.61 ml), and the resulted mixture was refluxed for 12 h. The reaction mixture was evaporated under reduced pressure followed by silica-gel column chromatography (chloroform : methanol= 50:1) to give 5-amino-4-ethoxycarbonyl-1-methylpyrazole (4.31 g, yield 84%).

To a solution of 5-amino-4-ethoxycarbonyl-1-methylpyrazole (0.845 g) in benzene (50 ml), were added phenyl isocyanate (0.543 ml) and triethylamine (0.70 ml), and the mixture was refluxed in a sealed tube for 3 h. The reaction mixture was evaporated under reduced pressure followed by repeated addition of ether, and the title compound was obtained as crystals (0.36 g, yield 25%).

$^1$H-NMR (CDCl$_3$) δ ppm: 1.31 (3H, t, J=7Hz, COOCH$_2$CH$_3$), 3.82 (3H, s, N—CH$_3$), 4.26 (2H, q, J=7Hz, COOCH$_2$CH$_3$), 7.40 (5H, m, Ph), 7.79 (1H, s, C3-H), 8.73 (2H, brs, NH×2)

Mass (m/z): 288 (M$^+$)

HRMS (m/z): C$_{14}$ H$_{16}$ N$_4$ O$_3$ calcd. 288.1222, found 288.1288 m.p.: 151°–153° C.

(EXAMPLE 6)

N-phenyl-N'-(4-ethoxycarbonyl-1-phenylpyrazol-5-yl)urea

The title compound was prepared by the similar method to Reference Example 2 (yield 50%).

$^1$H-NMR (CDCl$_3$) δ ppm: 1.33 (3H, t, J=7Hz, COOCH$_2$CH$_3$), 4.27 (2H, q, J=7Hz, COOCH$_2$CH$_3$), 7.40 (10H, m, Ph×2), 7.80 (1H, s, C3-H)

Mass (m/z): 350 (M$^+$)

HRMS (m/z): C$_{19}$ H$_{18}$ N$_4$ O$_3$ calcd. 350.1379, found 350.1475 m.p.: 184–185° C.

(EXAMPLE 7)

N-propyl-N'-(4-ethoxycarbonyl-1-phenylpyrazol-5-yl)urea

The title compound was prepared by the similar method to Reference Example 2 (yield 16%). $^1$H-NMR (CDCl$_3$) δ ppm: 0.83 (3H, t, J=7Hz, CH$_2$CH$_2$CH$_3$), 1.32 (3H, t, J=7Hz, COOCH$_2$CH$_3$), 1.45 (2H, 6th, CH$_2$CH$_2$CH$_3$), 3.15 (2H, q, J=5Hz, CH$_2$CH$_2$CH$_3$), 4.29 (2H, q, J=7Hz, COO CH$_2$CH$_3$), 6.79 (2H, brs, NH×2), 7.46 (5H, m, Ph), 8.21 (1H, s, C3-H)

Mass (m/z): 316 (M$^+$)

HRMS (m/z): C$_{16}$ H$_{20}$ N$_4$ O$_3$ calcd. 316.1535, found 316.1601 m.p.: 117°–118° C.

(EXAMPLE 8)

N-isopropyl-N'-(1-benzyl-4-ethoxycarbonylpyrazol-3-yl)urea

The title compound was prepared by the similar method to Reference Example 1 (yield 84%)

$^1$H-NMR (CDCl$_3$) δ ppm: 1.19 (6H, d, J=7Hz, —CH(CH$_3$)$_2$), 1.31 (3H, t, J=7Hz, COOCH$_2$CH$_3$), 3.99 (1H, m, —CH(CH$_3$)$_2$), 4.27 (2H, q, J=7Hz, COOCH$_2$CH$_3$), 5.13 (2H, s, N—CH$_2$Ph), 7.39 (5H, m, N—CH$_2$Ph), 7.67 (1H, s, C5-H), 7.78 (1H, brs, NH), 7.93 (1H, brs, NH)

Mass (m/z): 330 (M$^+$)

Anal.: C$_{17}$ H$_{22}$ N$_4$ O$_3$ calcd. C, 61.80; H, 6.71; N, 16.96 found. C, 61.87; H, 6.73; N, 16.96 m.p.: 111–112° C.

(EXAMPLE 9)

N-butyl-N'-(1-benzyl-4-ethoxycarbonylpyrazol-3-yl)urea

The title compound was prepared by the similar method to Reference Example 1 (yield 66%).

$^1$H-NMR (CDCl$_3$) δ ppm: 0.92 (3H, t, J=7Hz, —CH$_2$CH$_2$CH$_2$CH$_3$), 1.42 (7H, m, CH$_2$CH$_2$CH$_2$CH$_3$ and COOCH$_2$CH$_3$), 3.32 (2H, m, —CH$_2$CH$_2$CH$_2$CH$_3$), 5.14 (2H, s, N—CH$_2$Ph), 7.28 (5H, m, N—CH$_2$Ph), 7.67 (1H, s, C5-H), 7.99 (1H, brs, NH), 8.03 (1H, brs, NH)

Mass (m/z): 344 (M$^+$)

Anal.: C$_{18}$ H$_{24}$ N$_4$ O$_3$ calcd. C, 62.77; H, 7.02; N, 16.27 found. C, 62.63; H, 7.01; N, 16.27 m.p.: 104–105° C.

(EXAMPLE 10)

N-tert-butyl-N'-(1-benzyl-4-ethoxycarbonylpyrazol-3-yl)urea

The title compound was prepared by the similar method to Reference Example 1 (yield 85%)

$^1$H-NMR (CDCl$_3$) δ ppm: 1.31 (3H, t, J=7Hz, COOCH$_2$CH$_3$), 1.37 (9H, s, —C(CH$_3$)$_3$), 4.26 (2H, q, J=7Hz, COOCH$_2$CH$_3$), 5.11 (2H, s, N—CH$_2$Ph), 7.38 (5H, m, N—CH$_2$Ph), 7.68 (1H, s, C5-H), 7.82 (1H, brs, NH), 7.88 (1H, brs, NH)

Mass (m/z): 344 (M$^+$)

HRMS (m/z):C$_{18}$ H$_{24}$ N$_4$ O$_3$ calcd. 344.1848, found 344.1857 m.p.: 130–131° C.

(EXAMPLE 11)

N-2-propenyl-N'-(1-benzyl-4-ethoxycarbonylpyrazol-3-yl)urea

The title compound was prepared by the similar method to Reference Example 1 (yield 82%)

$^1$H-NMR (CDCl$_3$) δ ppm: 1.32 (3H, t, J=7Hz, COOCH$_2$CH$_3$), 3.98 (2H, t, J=2Hz, CH$_2$—CH=CH$_2$), 4.28 (2H, q, J=7Hz, COOCH$_2$CH$_3$), 5.10 (1H, dd, J=9Hz, 1Hz, —CH$_2$—CH=CHaHb), 5.15 (2H, s, N—CH$_2$Ph), 5.20 (1H, dd, J=6Hz, 1Hz, —CH$_2$—CH=CHaHb), 5.92 (1H, m, —CH$_2$—C$\underline{H}$=CH$_2$), 7.50 (5H, m, N—CH$_2$P$\underline{h}$), 7.66 (1H, s, C5-H), 8.02 (1H, brs, NH), 8.07 (1H, brs, NH)

Mass (m/z): 328 (M$^+$)

HRMS (m/z): C$_{17}$ H$_{20}$ N$_4$ O$_3$ calcd. 328.1535, found 328.1526 m.p.: 77–78° C.

(EXAMPLE 12)

N-cyclohexyl-N'-(1-benzyl-4-ethoxycarbonylpyrazol-3-yl)urea

The title compound was prepared by the similar method to Reference Example 1 (yield 76%).

$^1$H-NMR (CDCl$_3$) δ ppm: 1.27 (4H, m, c-hex), 1.31 (3H, t, J=7Hz, COOCH$_2$C$\underline{H_3}$), 1.57 (4H, m, c-hex), 1.90 (2H, m, c-hex), 3.80 (1H, m, c-hex), 4.27 (2H, q, J=7Hz, COOC$\underline{H_2}$CH$_3$), 5.13 (2H, s, N—C$\underline{H_2}$Ph), 7.39 (5H, m, N—CH$_2$P$\underline{h}$), 7.68 (1H, s, C5-H), 7.94 (2H, brs, each NH)

Mass (m/z): 370 (M$^+$)

HRMS (m/z): C$_{20}$ H$_{26}$ N$_4$ O$_3$ calcd. 370.2005, found 370.2020 m.p.: 94°–95° C.

(EXAMPLE 13)

N-benzyl-N'-(1-benzyl-4-ethoxycarbonylpyrazol-3-yl)urea

The title compound was prepared by the similar method to Reference Example 1 (yield 63%).

$^1$H-NMR (CDCl$_3$) δ ppm: 1.32 (3H, t, J=7Hz, COOCH$_2$C$\underline{H_3}$), 4.29 (2H, q, J=7Hz, COOC$\underline{H_2}$CH$_3$), 4.56 (2H, d, J=5Hz, 3NHCONHC$\underline{H_2}$Ph), 5.09 (2H, s, N—C$\underline{H_2}$Ph), 7.27 (10H, m, N—CH$_2$P$\underline{h}$ and 3NHCONHCH$_2$P$\underline{h}$), 7.66 (1H, s, C5-H), 8.11 (1H, s, NH), 8.31 (1H, brs, NH)

Mass (m/z): 378 (M$^+$)

Anal.: C$_{21}$ H$_{22}$ N$_4$ O$_3$ calcd. C, 66.65; H, 5.86; N, 14.80 found. C, 66.86; H, 5.87; N, 14.80 m.p.: 82°–83° C.

(EXAMPLE 14)

N, N-dimethyl-N'-(1-benzyl-4-ethoxycarbonylpyrazol-3-yl)urea

The title compound was prepared by the similar method to Reference Example 1 (yield 63%).

$^1$H-NMR (CDCl$_3$) δ ppm: 1.30 (3H, t, J=7Hz, COOCH$_2$C$\underline{H_3}$), 3.05 (6H, s, —N(C$\underline{H_3}$)$_2$), 4.24 (2H, q, J=7Hz, COOC$\underline{H_2}$CH$_3$), 5.26 (2H, s, N—C$\underline{H_2}$Ph), 7.42 (5H, m, N—CH$_2$P$\underline{h}$), 7.51 (1H, s, C5-H), 8.71 (1H, brs, NH)

Mass (m/z): 316 (M$^+$)

m.p.: 125°–126° C.

(EXAMPLE 15)

N, N-dipropyl-N'-(1-benzyl-4-ethoxycarbonylpyrazol-3-yl)urea

The title compound was prepared by the similar method to Reference Example 1 (yield 72%).

$^1$H-NMR (CDCl$_3$) δ ppm: 0.95 (6H, t, J=7Hz, —CH$_2$CH$_2$C$\underline{H_3}$×2), 1.29 (3H, t, J=7Hz, COOCH$_2$C$\underline{H_3}$), 1.70 (4H, m, —CH$_2$C$\underline{H_2}$CH$_3$×2), 3.30 (4H, t, J=7Hz, —C$\underline{H_2}$CH$_2$CH$_3$×2), 4.24 (2H, q, J=7Hz, COOC$\underline{H_2}$CH$_3$), 5.26 (2H, s, N—C$\underline{H_2}$Ph), 7.36 (5H, m, NCH$_2$P$\underline{h}$), 7.48 (1H, s, C5-H), 8.72 (1H, brs, NH)

Mass (m/z): 372 (M$^+$)

m.p.: 114°–115° C.

Anal. : C$_{20}$ H$_{28}$ N$_4$ O$_3$ calcd. C, 64.49; H, 7.58; N, 15.04 found. C, 64.20; H, 7.60; N, 14.82

(EXAMPLE 16)

N, N-diphenyl-N'-(1-benzyl-4-ethoxycarbonylpyrazol-3-yl)urea

The title compound was prepared by the similar method to Reference Example 1 (yield 3.3%).

$^1$H-NMR (CDCl$_3$) δ ppm: 1.12 (3H, t, J=7Hz, COOCH$_2$C$\underline{H_3}$), 4.02 (2H, q, J=7Hz, COOC$\underline{H_2}$CH$_3$), 5.25 (2H, s, N—C$\underline{H_2}$Ph), 7.30 (15H, m, N—CH$_2$P$\underline{h}$ and N(P$\underline{h}$)$_2$), 7.51 (1H, s, C5-H), 8.36 (1H, brs, NH)

Mass (m/z): 440 (M$^+$)

m.p. : 164°–165° C.

(EXAMPLE 17)

N-phenyl-N'-(4-ethoxycarbonylpyrazol-3-yl)urea

To a solution of 3-amino-4-ethoxycarbonylpyrazole (1.0 g) in THF (10 ml), was added di-tert-butyl dicarbonate (2.2 g), and the mixture was stirred overnight at room temperature. The reaction mixture was evaporated under reduced pressure followed by silica-gel column chromatography (toluene/ethyl acetate=15/1) to give 3-amino-1(tert-butoxycarbonyl)-4-ethoxycarbonylpyrazole (0.59 g). This intermediate was derived to N-phenyl-N'-(1-tert-butoxycarbonyl-4-ethoxycarbonylpyrazol-3-yl)urea by the similar method to Reference Example 1 (yield 75%). N-phenyl-N'-(1-tertbutoxycarbonyl-4-ethoxycarbonylpyrazol-3-yl)urea (0.5 g) was dissolved in a solution of 10% trifluoroacetic acid in dichloromethane (7 ml), and the resulted solution was stirred overnight at room temperature. The reaction mixture was evaporated under reduced pressure followed by addition of ether to give the title compound (0.304 g, yield 83%).

$^1$H-NMR (CDCl$_3$) δ ppm: 1.37 (3H, t, J=7Hz, COOCH$_2$C$\underline{H_3}$), 4.34 (2H, q, J=7Hz, COOC$\underline{H_2}$CH$_3$), 7.14 (1H, t, J=7Hz, p-Ph), 7.40 (2H, t, J=8Hz, m-Ph), 7.56 (2H, d, J=7Hz, o-Ph), 7.86 (brs, C5-H), 10.09 (brs, NH)

Mass (m/z): 274 (M$^+$)

m.p.: 257°–258° C.

Anal.: C$_{13}$ H$_{14}$ N$_4$ O$_3$ calcd. C, 56.93; H, 5.14; N, 20.43 found. C, 56.93; H, 5.11; N, 20.42

(EXAMPLE 18)

N-phenyl-N'-benzyl-N'-(1-benzyl-4-ethoxycarbonylpyrazol-3-yl)urea

To a solution of 3-amino-1benzyl-4-ethoxycarbonylpyrazole (0.5 g) in DMF (10 ml), was added 60% NaH (0.082 g). After stirring for 5 min at room temperature, benzyl bromide (0.307 ml) was added, and the mixture was stirred for 1 h at room temperature. The reaction mixture was evaporated under reduced pressure followed by silica-gel column chromatography (toluene/ ethyl acetate= 50/1) to give 3-benzylamino-1-benzyl-4-ethoxycarbonylpyrazole (0.3 g). This intermediate was derived to the title compound by the similar method to Reference Example 1 (yield 31%).

1H-NMR (CDCl$_3$) δ ppm: 1.26 (3H, t, J=7Hz, COOCH$_2$CH$_3$), 4.20 (2H, q, J=7Hz, COOCH$_2$CH$_3$), 5.04 (2H, s, 3—N—CH$_2$Ph ), 5.23 (2H, s, 1—CH$_2$Ph), 7.30 (15H, m, N—Ph, 3—N—CH$_2$Ph, and 1—CH$_2$Ph), 7.90 (1H, s, C5-H)

Mass (m/z): 454 (M$^+$)

m.p.: 116°–117° C.

Anal.: C$_{27}$ H$_{26}$ N$_4$ O$_3$ calcd. C, 71.35; H, 5.77; N, 12.33 found. C, 71.26; H, 5.83; N, 12.21

(EXAMPLE 19)

N-phenyl-N'-(1benzyl-4-ethoxycarbonylpyrazol-5-yl)urea

The title compound was prepared by the similar method to Reference Example 1 (yield 60%).

1H-NMR (CDCl$_3$) δ ppm: 1.28 (3H, t, J=7Hz, 4—COOCH$_2$CH$_3$), 4.20 (2H, q, J=7Hz, 4—COOCH$_2$CH$_3$), 5.48 (2H, s, N—CH$_2$Ph ), 7.23 (10H, m, N—CH$_2$Ph and N—Ph), 7.84 (1H, brs, NH), 7.87 (1H, s, C3-H)

Mass (m/z): 364 (M$^+$)

Anal.: C$_{20}$ H$_{20}$ N$_4$ O$_3$ calcd. C, 65.92; H, 5.53; N, 15.37 found. C, 65.82; H, 5.54; N, 15.29 m.p.: 178°–179° C.

(EXAMPLE 20)

N-cyclohexyl-N'-(1-benzyl-4-ethoxycarbonylpyrazol-5-yl)urea

The title compound was prepared by the similar method to Reference Example 1 (yield 96%)

1H-NMR (CDCl$_3$) δ ppm: 0.87–1.13 (6H, m, c-hex), 1.33 (3H, t, J=7Hz, 4—COOCH$_2$CH$_3$), 1.67 (2H, m, c-hex), 1.93 (2H, m, c-hex), 3.57 (1H, m, c-hex), 4.25 (2H, q, J=7Hz, 4—COOCH$_2$CH$_3$), 5.45 (2H, s, N—CH$_2$Ph), 7.24 (5H, in, N—CH$_2$Ph), 7.51 (1H, s, NH), 7.80 (1H, s, C3-H)

Mass (m/z): 370 (M$^+$)

m.p.: 182°–183° C.

(EXAMPLE 21)

N-(1-benzyl-4-ethoxycarbonylpyrazol-3-yl)urea

The title compound was prepared by the similar method to Reference Example 1 (yield 96%).

1H-NMR (CDCl$_3$) δ ppm: 1.32 (3H, t, 4—COOCH$_2$CH$_3$), 4.29 (2H, q, 4—COOCH$_2$CH$_3$), 5.16 (2H, S, N—CH$_2$Ph), 7.45 (5H, m, N—CH$_2$Ph), 7.67 (1H, s, C5-H), 8.15 (1H, brs, NH)

Mass (m/z): 288 (M$^+$)

Anal.: C$_{14}$ H$_{16}$ N$_4$ O$_3$·⅓ H$_2$O calcd. C, 57.61; H, 5.66; N, 19.19 found. C, 57.73; H, 5.56; N, 19.19 m.p.: 156°–157° C.

(EXAMPLE 22)

Inhibiting effect on PDGF-stimulated cell growth

Effect on PDGF-stimulated cell growth was estimated by the following method using fibroblasts, growth of which is induced by PDGF in the same manner of smooth muscle cells to verify inhibitory activity of the pyrazole derivative of the present invention against PDGF-stimulated cell growth.

(Test method)

BALB/c 3T3 cells seeded on a 96-well plate (3–5×10$^3$ cell/well) were incubated in a high glucose Dulbecco's modified Eagle's medium (DME medium) containing 10% fetal bovine sera (FBS) for 2–3 days until confluent. The medium was replaced by high glucose DME medium containing 0.5% platelet poor plasma (PPP) followed by incubation for further 24 h.

The medium was replaced by high glucose DME medium containing PDGF-AA or PDGF-BB (10 ng/mL) to induce PDGF-stimulated cell growth, and a DMSO solution of a test sample was added followed by incubation for 16 h. Then, $^3$H-thymidine (1 mCi/ml) was 20-fold diluted by Ca$^{2+}$ and Mg$^{2+}$ free phosphate-bufferized saline, and 0.02 mL of the resulted solution was added followed by incubation for further 4 h. Final concentration of DMSO was not more than 0.25%.

After $^3$H-thymidine in the medium was washed out, cells were treated with trypsin/EDTA and collected using a cell-harvester. Amount of $^3$H-thymidine taken in the cells was measured by a liquid scintillation counter. Reference incubation was performed under the similar condition without adding a test compound, and amount of $^3$H-thymidine taken in the cells was measured. Growth inhibition was estimated by difference of the amount of $^3$H-thymidine taken between the test incubation and the reference incubation.

Results for the pyrazole derivatives of the present invention are exemplified on Table 1. Trapidil [7-diethylamino-5-methyltriazolo [1,5-a]pyrimidine: e.g. Life Sciences, 28, 1641–1646 (1981)] and tranilast [N-(3,4-dimethoxycinnamoyl) anthranilic acid: e.g. Rinsho Iyaku, 12, 65–85 (1996)], which have been reported to inhibit PDGF-stimulated smooth muscle cell growth, were used as positive references.

TABLE 1

| Compound | concentration (μM) | inhibition (%) |
| --- | --- | --- |
| Example 1 | 3 | 84.5 |
| Example 2 | 3 | 81.9 |
| Example 3 | 3 | 89.5 |
| Example 6 | 3 | 49.9 |
| Example 7 | 3 | 36.4 |
| [positive reference] | | |
| trapidil | 50 | 46.6 |
| tranilast | 10 | 19.2 |
|  | 30 | 57.1 |
|  | 100 | 92.5 |

0.1 mM or less of the pyrazole derivatives of the present invention did not inhibit natural cell growth in the absence of growth factor such as PDGF.

(EXAMPLE 23)

Pharmaceutical formulation

As the inhibitor of smooth muscle cell growth, tablets can be prepared as follows. The compound of Example 1 was used as the active ingredient, and 100 mg tablets were prepared by a usual manner in a formulation of the following Table 2.

TABLE 2

| compound of Example 1 | 10 g |
|---|---|
| lactose | 100 g |
| corn starch | 50 g |
| poly(vinylpyrrolidone) | 20 g |

(EXAMPLE 24)

Inhibiting effect on PDGF-stimulated smooth muscle cell growth

Effect on PDGF-stimulated smooth muscle cell growth was estimated by the following method to verify inhibitory activity of the pyrazole derivative of the present invention against smooth muscle cell growth. (Test method)

Human coronary artery smooth muscle cells seeded on a 96-well plate ($2 \times 10^4$ cell/well) were incubated in a complete medium consisting of a basal medium (SmGM-2: Iwaki Glass Co., Japan), FBS (5%), EGF (0.5 ng/mL), insulin (0.005 mg/mL), and basic-FGF (2 ng/mL) for 24 h until confluent. The medium was replaced by the basal medium followed by incubation for further 24 h to lead cells to G0 stage.

The medium was replaced by a medium consisting of the basal medium and PDGF-BB (20 ng/mL) to induce PDGF-stimulated cell growth, and a DMSO solution of a test sample was added followed by incubation for 16 h. Then, inhibition of cell growth was estimated by a $^3$H-thymidine method as described in Example 22.

Results for the pyrazole derivatives of the present invention are exemplified on Table 3. Tranilast was used as positive reference.

TABLE 3

| Compound | IC50 ($\mu$M) |
|---|---|
| Example 1 | 2.3 |
| Example 2 | 3.1 |
| Example 3 | 1.5 |
| Example 8 | 1.3 |
| Example 15 | 2.2 |
| Example 16 | 1.1 |
| Example 18 | 3.0 |
| Tranilast | 5.0 |

0.01 mM or less of the pyrazole derivatives of the present invention did not inhibit natural cell growth in the presence of 10% FBS.

What is claimed is:

1. A pyrazole derivative represented by the following general formula (I) or the following general formula (II):

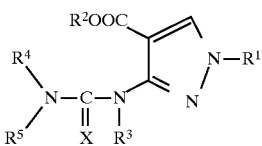

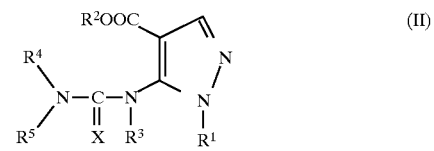

wherein $R^1$ is a hydrogen atom, a linear or branched C2–C6 alkyl group, a benzyl group, or a phenyl group; each of $R^2$ and $R^3$ is a hydrogen atom, a linear or branched C1–C6 alkyl group, or a benzyl group; each of $R^4$ and $R^5$ is a hydrogen atom, a linear or branched C1–C6 alkyl group, a linear or branched C3–C6 alkenyl group, a C3–C8 cycloalkyl group, a benzyl group, or a phenyl group;

X is an oxygen atom or a sulfur atom;

$R^5$ is a hydrogen atom, a linear or branched C2–C6 alkyl group, a linear or branched C3–C6 alkenyl group, a C3–C8 cycloalkyl group, or a benzyl group when $R^1$ is a benzyl group, $R^2$ is an ethyl group, $R^3$ is a hydrogen-atom, and $R^4$ is a hydrogen atom, or a pharmaceutically acceptable salt thereof.

2. The compound of claim 1, which is represented by the general formula (I) wherein $R^1$ is a linear or branched C2–C6 alkyl group, or a benzyl group.

3. The compound of claim 1, which is represented by the general formula (I) wherein at least one of $R^4$ and $R^5$ is not a hydrogen atom.

4. The compound of claim 1, which is represented by the general formula (II) wherein $R^1$ is a linear or branched C2–C6 alkyl group, a benzyl group, or a phenyl group.

5. The compound of claim 1, which is represented by the general formula (II) wherein at least one of $R^4$ and $R^5$ is not a hydrogen atom.

6. A method for inhibiting smooth muscle cell growth comprising: employing the compound of claim 1.

7. A pharmaceutical composition comprising the compound of claim 1 and a pharmaceutically acceptable carrier for prevention or cure of diseases caused by smooth muscle cell growth.

8. A pharmaceutical composition of claim 7 in which the diseases caused by smooth muscle cell growth is vascular re-narrowing after percutaneous transluminal coronary angioplasty, vascular re-narrowing after percutaneous transluminal angioplasty, membrane proliferative nephritis, arteriosclerotic diseases, hypertension, or diabetes mellitus.

* * * * *